United States Patent
Yanev et al.

(10) Patent No.: US 9,230,064 B2
(45) Date of Patent: Jan. 5, 2016

(54) PERSONAL WELLNESS DEVICE

(75) Inventors: Kostadin Dimitrov Yanev, Alamo, CA (US); Angel Georgiev Vassilev, Sofia (BG); Ivo Kostadinov Yanev, Sofia (BG); Kamen Radev Dobrev, Varna (BG)

(73) Assignee: EZ AS A DRINK PRODUCTIONS, INC., Reno, NV (US)

( * ) Notice: Subject to any disclaimer, the term of this patent is extended or adjusted under 35 U.S.C. 154(b) by 279 days.

(21) Appl. No.: 13/527,465

(22) Filed: Jun. 19, 2012

(65) Prior Publication Data

US 2013/0337976 A1    Dec. 19, 2013

(51) Int. Cl.
*A63B 21/002*    (2006.01)
*A63B 71/00*    (2006.01)
(Continued)

(52) U.S. Cl.
CPC .............. *G06F 19/3481* (2013.01); *A61B 5/02* (2013.01); *A61B 5/103* (2013.01); *A61B 5/14532* (2013.01); *A61B 5/4528* (2013.01); *A61B 5/74* (2013.01); *A63B 21/002* (2013.01); *A61B 2505/09* (2013.01); *A61N 1/36003* (2013.01); *A63B 2220/51* (2013.01); *A63B 2220/56* (2013.01)

(58) Field of Classification Search
CPC .............. A63B 24/00; A63B 2220/00; A63B 21/1492; A63B 21/1496; A63B 23/16; A63B 2220/51; A63B 2220/56; A61B 5/22
USPC ..................................................... 482/1, 8, 9
See application file for complete search history.

(56) References Cited

U.S. PATENT DOCUMENTS

| 4,577,625 A | 3/1986 | Lohati et al. ..................... 128/57 |
| 4,702,108 A | 10/1987 | Amundsen et al. ............. 73/379 |

(Continued)

FOREIGN PATENT DOCUMENTS

| CN | 201270095 | 8/2009 |
| EP | 2 284 646 | 2/2011 |

(Continued)

OTHER PUBLICATIONS

"Fitness Made Fun", Instruction Booklet, copyright 2008 Nintendo, 28 pages.

(Continued)

*Primary Examiner* — Loan H Thanh
*Assistant Examiner* — Sundhara Ganesan
(74) *Attorney, Agent, or Firm* — Pillsbury Winthrop Shaw Pittman, LLP

(57) ABSTRACT

A personal wellness device comprise two housing bodies, a force sensor, a user interface, one or more processors, and/or other components. A first housing body and a second housing body may be movably coupled together by way of a coupling mechanism such that the two housing bodies are reconfigurable between an open configuration and a closed configuration. The force sensor may be configured to generate a force output signal that conveys information related to compressive force exerted on the two housing bodies while in the closed configuration. The user interface may be accessible with the two housing bodies in the open configuration. The one or more processors may be configured to execute one or more computer program modules, including a presentation module configured to present, via the user interface, information associated with compressive force exerted on the two housing bodies, the information being derived from the force output signal.

22 Claims, 7 Drawing Sheets

(51) Int. Cl.
*G06F 19/00* (2011.01)
*A61B 5/103* (2006.01)
*A61B 5/00* (2006.01)
*A61B 5/02* (2006.01)
*A61B 5/145* (2006.01)
*A61N 1/36* (2006.01)

(56) References Cited

U.S. PATENT DOCUMENTS

| | | | |
|---|---|---|---|
| 4,824,103 A | 4/1989 | Smidt | 272/125 |
| 4,988,981 A | 1/1991 | Zimmerman | |
| 5,144,284 A | 9/1992 | Hammett | 340/573 |
| 5,242,348 A | 9/1993 | Bates | 482/105 |
| 5,471,405 A | 11/1995 | Marsh | 364/556 |
| 5,702,323 A | 12/1997 | Poulton | |
| 5,720,711 A * | 2/1998 | Bond et al. | 601/23 |
| 5,790,102 A | 8/1998 | Nassimi | 345/163 |
| 5,792,080 A | 8/1998 | Ookawa et al. | 601/115 |
| 5,890,995 A | 4/1999 | Bobick et al. | 482/4 |
| 5,904,639 A | 5/1999 | Smyser et al. | 482/91 |
| 5,923,318 A | 7/1999 | Zhai et al. | |
| 5,982,342 A | 11/1999 | Iwata | |
| 5,997,489 A | 12/1999 | Iwamoto et al. | 601/73 |
| 6,013,007 A | 1/2000 | Root et al. | 482/8 |
| 6,063,045 A | 5/2000 | Wax | |
| 6,126,572 A | 10/2000 | Smith | 482/4 |
| 6,183,425 B1 | 2/2001 | Whalen et al. | 600/592 |
| 6,191,773 B1 | 2/2001 | Maruno | |
| 6,222,465 B1 | 4/2001 | Kumar | |
| 6,227,968 B1 | 5/2001 | Suzuki et al. | 463/7 |
| 6,324,557 B1 * | 11/2001 | Chan | 708/142 |
| 6,359,611 B2 | 3/2002 | Chan | 345/156 |
| 6,360,597 B1 | 3/2002 | Hubbard, Jr. | 73/172 |
| 6,405,278 B1 | 6/2002 | Liepe | 711/103 |
| 6,435,937 B1 * | 8/2002 | Naegele | 446/298 |
| 6,513,532 B2 | 2/2003 | Mault et al. | 128/921 |
| 6,585,668 B2 | 7/2003 | Nissim | 601/84 |
| 6,595,901 B2 | 7/2003 | Reinbold et al. | 482/91 |
| 6,597,347 B1 | 7/2003 | Yasutake | |
| 6,605,038 B1 | 8/2003 | Teller et al. | 600/300 |
| 6,616,579 B1 | 9/2003 | Reinbold et al. | 482/8 |
| 6,662,651 B1 * | 12/2003 | Roth | 73/379.02 |
| 6,675,130 B2 | 1/2004 | Kanevsky et al. | 702/188 |
| 6,776,345 B1 | 8/2004 | Liang | 235/486 |
| 6,807,869 B2 | 10/2004 | Farringdon et al. | 73/862.046 |
| 6,837,827 B1 | 1/2005 | Lee et al. | 482/8 |
| 6,914,695 B2 | 7/2005 | Walters et al. | 358/1.15 |
| 6,956,833 B1 | 10/2005 | Yukie et al. | 370/328 |
| 6,975,644 B2 | 12/2005 | Tordera et al. | 370/463 |
| 7,026,940 B2 | 4/2006 | Cherubini | 340/573.1 |
| 7,121,982 B2 | 10/2006 | Feldman | 482/8 |
| 7,161,490 B2 | 1/2007 | Huiban | 340/573.1 |
| 7,169,120 B2 | 1/2007 | Murdock et al. | 601/129 |
| 7,192,387 B2 * | 3/2007 | Mendel | 482/8 |
| 7,229,385 B2 | 6/2007 | Freeman et al. | 482/4 |
| 7,292,867 B2 | 11/2007 | Werner et al. | 455/456.3 |
| 7,303,534 B2 | 12/2007 | Kahn | 600/587 |
| 7,398,151 B1 | 7/2008 | Burrell et al. | 701/200 |
| 7,429,251 B2 | 9/2008 | Tanizawa et al. | 601/94 |
| 7,468,968 B2 | 12/2008 | Svensson et al. | 370/338 |
| 7,480,512 B2 | 1/2009 | Graham et al. | 455/456.3 |
| 7,499,746 B2 | 3/2009 | Buhlmann et al. | 607/2 |
| 7,517,327 B1 | 4/2009 | Knight | 601/46 |
| 7,526,314 B2 | 4/2009 | Kennedy | 455/556.1 |
| 7,526,954 B2 | 5/2009 | Haselhurst et al. | 73/172 |
| RE40,891 E | 9/2009 | Yasutake | |
| 7,643,895 B2 | 1/2010 | Gupta et al. | 700/94 |
| 7,666,118 B1 | 2/2010 | Anthony | 482/8 |
| 7,699,755 B2 | 4/2010 | Feldman et al. | 482/8 |
| 7,699,757 B2 * | 4/2010 | Clem et al. | 482/49 |
| 7,702,821 B2 | 4/2010 | Feinberg et al. | 710/13 |
| 7,717,825 B2 | 5/2010 | Van Der Hoeven | 482/8 |
| 7,758,469 B2 | 7/2010 | Dyer et al. | 482/4 |
| 7,789,800 B1 | 9/2010 | Watterson et al. | 482/8 |
| 7,840,346 B2 * | 11/2010 | Huhtala et al. | 701/439 |
| 7,909,741 B2 | 3/2011 | Kim et al. | 482/93 |
| 7,975,543 B2 * | 7/2011 | Clem et al. | 73/379.02 |
| 8,009,056 B2 | 8/2011 | Greene | 340/667 |
| 8,025,606 B2 | 9/2011 | Hamilton | 482/4 |
| 8,027,822 B2 | 9/2011 | Turgiss et al. | 703/11 |
| 8,172,723 B1 | 5/2012 | Yanev et al. | 482/8 |
| 8,200,323 B2 * | 6/2012 | DiBenedetto et al. | 600/519 |
| 8,203,454 B2 | 6/2012 | Knight et al. | 340/573.1 |
| 8,287,434 B2 | 10/2012 | Zavadsky et al. | 482/5 |
| 8,343,013 B1 | 1/2013 | Yanev et al. | 482/8 |
| 8,491,446 B2 | 7/2013 | Hinds et al. | 482/8 |
| 8,618,400 B2 | 12/2013 | Murphy et al. | 84/600 |
| 8,935,438 B1 | 1/2015 | Ivanchenko | 710/16 |
| 2001/0049470 A1 | 12/2001 | Mault et al. | 600/300 |
| 2002/0146670 A1 | 10/2002 | Selles et al. | 434/247 |
| 2003/0020629 A1 | 1/2003 | Swartz et al. | 340/825.25 |
| 2003/0040688 A1 | 2/2003 | Bauer | 601/23 |
| 2003/0093012 A1 | 5/2003 | Smyser | |
| 2003/0137495 A1 | 7/2003 | Canova, Jr. | 345/173 |
| 2004/0021681 A1 | 2/2004 | Liao | 345/702 |
| 2004/0058305 A1 | 3/2004 | Lurie et al. | 434/265 |
| 2004/0110602 A1 | 6/2004 | Feldman | |
| 2004/0176226 A1 | 9/2004 | Carlson | |
| 2004/0260215 A1 | 12/2004 | Kim | 601/99 |
| 2005/0040999 A1 | 2/2005 | Numano | 345/1.1 |
| 2005/0130742 A1 | 6/2005 | Feldman et al. | 463/39 |
| 2005/0177054 A1 | 8/2005 | Yi et al. | |
| 2005/0209049 A1 * | 9/2005 | Shields | 482/8 |
| 2005/0219355 A1 * | 10/2005 | Tahara et al. | 348/14.05 |
| 2005/0283204 A1 | 12/2005 | Buhlmann | |
| 2006/0035762 A1 | 2/2006 | Smyser et al. | 482/91 |
| 2006/0064042 A1 * | 3/2006 | Smyser et al. | 600/595 |
| 2006/0100899 A1 | 5/2006 | Tajima | 705/2 |
| 2006/0122819 A1 | 6/2006 | Carmel | |
| 2006/0247095 A1 * | 11/2006 | Rummerfield | 482/1 |
| 2007/0015589 A1 | 1/2007 | Shimizu | |
| 2007/0024736 A1 | 2/2007 | Matsuda et al. | 348/333.12 |
| 2007/0051842 A1 | 3/2007 | Pryor | 242/378.3 |
| 2007/0184953 A1 | 8/2007 | Luberski et al. | 482/146 |
| 2007/0219059 A1 | 9/2007 | Schwartz et al. | 482/8 |
| 2007/0219469 A1 | 9/2007 | Vardy | 600/587 |
| 2007/0232455 A1 | 10/2007 | Hanoun | |
| 2007/0249975 A1 | 10/2007 | Pan et al. | 601/118 |
| 2007/0270727 A1 | 11/2007 | KhorassaniZadeh | |
| 2008/0090703 A1 | 4/2008 | Rosenberg | 492/8 |
| 2008/0091762 A1 | 4/2008 | Neuhauser et al. | 709/201 |
| 2008/0096726 A1 | 4/2008 | Riley et al. | 482/8 |
| 2008/0100718 A1 | 5/2008 | Louks et al. | 348/211.2 |
| 2008/0101272 A1 | 5/2008 | Hayes et al. | 370/313 |
| 2008/0132388 A1 | 6/2008 | Clem | |
| 2008/0146336 A1 | 6/2008 | Feldman et al. | 463/37 |
| 2008/0161051 A1 | 7/2008 | Schobbert et al. | 455/558 |
| 2008/0171311 A1 | 7/2008 | Centen et al. | 434/265 |
| 2008/0261696 A1 | 10/2008 | Yamazaki et al. | 463/39 |
| 2008/0262918 A1 | 10/2008 | Wiener | 705/14 |
| 2008/0281234 A1 | 11/2008 | Goris et al. | 600/595 |
| 2008/0287832 A1 | 11/2008 | Collins et al. | 600/587 |
| 2008/0300055 A1 | 12/2008 | Lutnick | |
| 2009/0017993 A1 * | 1/2009 | Khanicheh et al. | 482/49 |
| 2009/0025475 A1 | 1/2009 | DeBeliso et al. | 73/379.02 |
| 2009/0035740 A1 | 2/2009 | Reed et al. | 434/265 |
| 2009/0048021 A1 | 2/2009 | Lian et al. | 463/37 |
| 2009/0048070 A1 | 2/2009 | Vincent et al. | 482/8 |
| 2009/0069160 A1 * | 3/2009 | Summers | 482/91 |
| 2009/0076855 A1 | 3/2009 | McCord | 705/3 |
| 2009/0144080 A1 | 6/2009 | Gray et al. | 705/2 |
| 2009/0148821 A1 | 6/2009 | Carkner et al. | 434/265 |
| 2009/0228068 A1 | 9/2009 | Buhlmann et al. | 607/48 |
| 2009/0286654 A1 | 11/2009 | Rice | 482/4 |
| 2010/0021876 A1 | 1/2010 | Clash | 434/265 |
| 2010/0056341 A1 * | 3/2010 | Ellis et al. | 482/9 |
| 2010/0069148 A1 | 3/2010 | Cargill | 463/25 |
| 2010/0087763 A1 | 4/2010 | Hane-Karr | 601/137 |
| 2010/0127983 A1 | 5/2010 | Irani et al. | 345/163 |
| 2010/0137105 A1 * | 6/2010 | McLaughlin | 482/8 |
| 2010/0178981 A1 * | 7/2010 | Holcomb et al. | 463/37 |
| 2010/0197462 A1 | 8/2010 | Piane, Jr. | 482/5 |
| 2010/0245239 A1 | 9/2010 | Sternberg | 345/156 |

(56) References Cited

U.S. PATENT DOCUMENTS

| | | | |
|---|---|---|---|
| 2010/0248822 A1 | 9/2010 | Migos et al. ..................... 463/29 |
| 2010/0255862 A1 | 10/2010 | Mitsunaga et al. ............ 455/466 |
| 2010/0255957 A1 | 10/2010 | Clem et al. ...................... 482/49 |
| 2010/0259472 A1 | 10/2010 | Radivojevic et al. .......... 345/156 |
| 2010/0265179 A1 | 10/2010 | Ram .............................. 345/163 |
| 2010/0273610 A1* | 10/2010 | Johnson ............................ 482/9 |
| 2010/0292050 A1 | 11/2010 | DiBenedetto et al. ............ 482/9 |
| 2010/0292600 A1* | 11/2010 | DiBenedetto et al. ......... 600/520 |
| 2011/0035303 A1 | 2/2011 | Jakstadt et al. .................. 705/34 |
| 2011/0046687 A1 | 2/2011 | Naschberger ..................... 607/3 |
| 2011/0086747 A1 | 4/2011 | Broderick ...................... 482/142 |
| 2011/0124470 A1* | 5/2011 | Spurling et al. ................. 482/13 |
| 2011/0125866 A1* | 5/2011 | Williams ....................... 709/217 |
| 2011/0143769 A1 | 6/2011 | Jones et al. ................. 455/456.1 |
| 2011/0165998 A1* | 7/2011 | Lau et al. ........................... 482/8 |
| 2011/0187660 A1 | 8/2011 | Hirata et al. ................... 345/173 |
| 2011/0251021 A1 | 10/2011 | Zavadsky et al. ................. 482/5 |
| 2011/0260987 A1 | 10/2011 | Zhao et al. .................... 345/173 |
| 2011/0291943 A1 | 12/2011 | Thorn et al. .................. 345/173 |
| 2011/0302694 A1 | 12/2011 | Wang et al. ....................... 2/160 |
| 2012/0047465 A1 | 2/2012 | Noda |
| 2012/0051596 A1 | 3/2012 | Darnell |
| 2012/0058861 A1 | 3/2012 | Satut ................................ 482/8 |
| 2012/0066591 A1 | 3/2012 | Hackwell ...................... 715/702 |
| 2012/0071732 A1 | 3/2012 | Grey et al. ..................... 600/301 |
| 2012/0075236 A1 | 3/2012 | Kim et al. ..................... 345/174 |
| 2012/0077163 A1 | 3/2012 | SucarSuccar |
| 2012/0078113 A1 | 3/2012 | Whitestone et al. .......... 600/474 |
| 2012/0088553 A1 | 4/2012 | Nunes ........................... 455/566 |
| 2012/0098744 A1 | 4/2012 | Stinson, III ................... 345/158 |
| 2012/0108394 A1* | 5/2012 | Jones et al. ....................... 482/8 |
| 2012/0112922 A1* | 5/2012 | Hillis et al. ................... 340/657 |
| 2012/0113019 A1 | 5/2012 | Anderson ...................... 345/173 |
| 2012/0116550 A1 | 5/2012 | Hoffman et al. ................ 700/91 |
| 2012/0126941 A1 | 5/2012 | Coggill ......................... 340/5.54 |
| 2012/0150074 A1 | 6/2012 | Yanev et al. .................. 600/300 |
| 2012/0162080 A1 | 6/2012 | Cao ............................... 345/168 |
| 2012/0260220 A1 | 10/2012 | Griffin .......................... 715/863 |
| 2012/0265112 A1 | 10/2012 | Chen .............................. 601/115 |
| 2012/0274508 A1 | 11/2012 | Brown |
| 2012/0306782 A1 | 12/2012 | Seo et al. ....................... 345/173 |
| 2013/0009907 A1 | 1/2013 | Rosenberg et al. ........... 345/174 |
| 2013/0059696 A1* | 3/2013 | Hijmans et al. .................. 482/8 |
| 2013/0072301 A1 | 3/2013 | Mallinson |
| 2013/0076649 A1 | 3/2013 | Myers et al. .................. 345/173 |
| 2013/0093679 A1* | 4/2013 | Dickinson et al. ............ 345/168 |
| 2013/0106155 A1 | 5/2013 | Chang ......................... 297/217.3 |
| 2013/0127748 A1 | 5/2013 | Vertegaal et al. ............. 345/173 |
| 2013/0127980 A1 | 5/2013 | Haddick |
| 2013/0201316 A1 | 8/2013 | Binder |
| 2013/0212674 A1 | 8/2013 | Boger |
| 2013/0337974 A1 | 12/2013 | Yanev et al. ...................... 482/8 |
| 2013/0337975 A1 | 12/2013 | Yanev et al. ...................... 482/8 |
| 2013/0344919 A1 | 12/2013 | Kim et al. ..................... 455/566 |
| 2013/0345608 A1 | 12/2013 | Ehrenreich |
| 2014/0062682 A1 | 3/2014 | Birnbaum |
| 2014/0123003 A1 | 5/2014 | Song .............................. 715/70 |
| 2014/0184496 A1 | 7/2014 | Gribetz |
| 2014/0317722 A1 | 10/2014 | Tartz et al. ..................... 726/19 |
| 2014/0333543 A1 | 11/2014 | Yanev et al. .................. 345/173 |
| 2014/0335494 A1 | 11/2014 | Yanev et al. .................. 434/262 |
| 2015/0015476 A1 | 1/2015 | Yanev et al. .................. 345/156 |
| 2015/0173993 A1 | 6/2015 | Walsh |

FOREIGN PATENT DOCUMENTS

| | | |
|---|---|---|
| JP | 2006345990 | 12/2006 |
| JP | 2009142333 | 7/2009 |
| JP | 2010524094 | 7/2010 |
| JP | 2013/172841 | 9/2013 |
| TW | 509566 | 1/1988 |
| TW | 201000175 A | 1/2010 |
| TW | 201300098 | 1/2013 |
| TW | 201301215 | 1/2013 |
| WO | WO 2007/025382 | 3/2007 |
| WO | WO 2012/078718 | 6/2012 |
| WO | WO 2013/192071 | 12/2013 |
| WO | WO 2013/192079 | 12/2013 |
| WO | WO 2013/192084 | 12/2013 |
| WO | 2014018049 | 1/2014 |
| WO | WO 2014/182729 | 11/2014 |
| WO | WO 2014/182735 | 11/2014 |
| WO | WO 2015/006411 | 1/2015 |
| WO | WO 2015/006413 | 1/2015 |

OTHER PUBLICATIONS

Jovanov et al., "A Wireless Body Area Network of Intelligent Motion Sensors for Computer Assisted Physical Rehabilitation", Journal of NeuroEngineering and Rehabilitation, Mar. 1, 2005, vol. 2, No. 6, retrieved from URL: http://www.jneuroengrehab.com/content/2/1/6, retrieved on Apr. 2, 2012, 10 pages.

Halfbakery, "Computer Mouse with Pressure Sensitive Button", printed from http://www.halfbakery.com/idea/Computer_20Mouse_20with_20pressure..., Cord, May 10, 2005, printed Apr. 4, 2014, 3 pages.

International Search Report and Written Opinion mailed Apr. 20, 2012 for corresponding International Patent Application No. PCT/US2011/063678 (7 pages).

International Search Report and Written Opinion mailed Oct. 1, 2013 for corresponding International Patent Application No. PCT/US2013/046096 (10 pages).

International Search Report and Written Opinion mailed Oct. 2, 2013 for corresponding International Patent Application No. PCT/US2013/046118 (10 pages).

International Search Report and Written Opinion mailed Nov. 22, 2013 for corresponding International Patent Application No. PCT/US2013/046082 (7 pages).

International Search Report and Written Opinion mailed Nov. 7, 2014 for corresponding International Patent Application No. PCT/US2014/045899 (7 pages).

International Search Report and Written Opinion mailed Mar. 4, 2015 for corresponding International Patent Application No. PCT/US2014/037018, 9 pages.

International Search Report and Written Opinion mailed Mar. 13, 2015 for corresponding International Patent Application No. PCT/US2014/037012, 9 pages.

\* cited by examiner

PERSONAL WELLNESS DEVICE

FIELD OF THE INVENTION

The invention relates to a portable device configured to facilitate personal exercise using the device and to promote personal wellness by determining and/or evaluating aspects of personal health and/or exercise.

BACKGROUND OF THE INVENTION

Apparatus used during personal exercise are typically considered either stationary or portable. Stationary apparatus may be configured to quantify various aspects of an exercise routine, such as number of repetitions, calories burnt, etc. Portable apparatus generally include much less functionality relative to larger, stationary apparatus.

SUMMARY

One aspect of the invention relates to a personal wellness system configured to facilitate personal wellness via a personal wellness device, in accordance with one or more implementations. The personal wellness device may be a portable, handheld device configured to facilitate personal exercise using the device. In some implementations, compressive forces exerted on the personal wellness device may be measured and/or recorded through the use of a force sensor included in the personal wellness device. Geo-location and/or motion of personal wellness device may be utilized in measuring and/or recording personal exercises performed with the personal wellness device. Steps taken and/or distance traveled may be determined, in some implementations, by use of a pedometer included in the personal wellness device. Therapy such as electrical muscle stimulation (EMS) may be facilitated by the personal wellness device.

The personal wellness device may promote personal wellness by determining and/or evaluating aspects of personal health and/or exercise. By way of non-limiting example, aspects of personal health may include vital signs, trends in personal fitness, frequency of exercise, and/or other aspects of personal health, while aspects of personal exercise may include number of repetitions, calories burnt, duration of exercise, and/or other aspects of personal exercise. In some implementation, the personal wellness device may facilitate personal wellness management.

The personal wellness device may be configured to facilitate interpersonal communications, such as voice over internet protocol, short message service, multimedia messaging service, video conferencing, telephony, and/or other interpersonal communications. The personal wellness device may facilitate socializing and/or merchandizing, according to some implementations.

In addition to the personal wellness device, the personal wellness system may include one or more of a user accessory, external resources, a personal computing platform, a personal wellness platform server, and/or other components, which may complement and/or include one or more functionalities attributed herein to the personal wellness device. Components of the personal wellness system, such as the personal wellness device, the personal computing platform, the personal wellness platform server, the user accessory, and/or external resources, may be operatively linked via one or more electronic communication links.

The personal wellness device may include one or more of a force sensor, a geo-location sensor, a motion sensor, a heart rate sensor, a blood glucose sensor, a biometric sensor, a pedometer, an electrical muscle stimulation (EMS) interface, a camera device, an actuator, a user interface, the communications apparatus, a power supply, the electronic storage, a processor, and/or other components. One or more components of the personal wellness device may be housed by one or more housing bodies. In implementations having two housing bodies, a first housing body and a second housing body may be movably coupled together by way of a coupling mechanism such that the two housing bodies are reconfigurable between an open configuration and a closed configuration. The two housing bodies may be configured to receive compressive force during personal exercise while in the closed configuration.

The force sensor may be configured to generate a force output signal that conveys information related to compressive force exerted on the personal wellness device. Such information may include or be used to determine magnitude of force, duration of force, a force magnitude profile as a function of time, a quantity of compressive forces, and/or other information related to compressive force exerted on the personal wellness device. The force output signal generated by the force sensor may be received and/or utilized by one or more modules executable by the processor, as described further herein.

The geo-location sensor may be configured to generate a location output signal conveying information related to a geo-location of the personal wellness device. The location output signal may be used to quantify one or more parameters of personal exercise. Such parameters may include speed, distance traveled, course of travel, and/or other parameters related to a geo-location of the personal wellness device.

The motion sensor may be configured to generate a motion output signal that conveys information related to a motion and/or orientation of the personal wellness device. The motion output signal may be used to quantify motions, changes in motion, orientation, changes in orientation, and/or information derived therefrom.

The heart rate sensor may be configured to generate a heart rate output signal that conveys information related to a heart rate of a user associated with the personal wellness device. The heart rate sensor may utilize electrocardiography (ECG or EKG). The heart rate output signal may be used to monitor heart rate in real time or record heart rate data for later observation and/or analysis. In some implementations, the heart rate sensor is integrated into the personal wellness device such that the heart rate sensor may measure a user's heart rate by way of physical contact between the user and the personal wellness device. The heart rate sensor may communicatively couple with a heart rate monitor that is separate and distinct from the personal wellness device, according to some implementations.

The blood glucose sensor may be configured to generate a glucose output signal that conveys information related to a concentration of glucose in the blood of a user associated with the personal wellness device. The glucose output signal may be used to determine a concentration of glucose and/or information derived therefrom. In some implementations, the blood glucose sensor may require a blood sample from a user in order to generate the glucose output signal. The blood glucose sensor may be based on one or more non-invasive technologies including near IR detection, ultrasound, dielectric spectroscopy, and/or other non-invasive technologies for determining glucose concentration, in accordance with some implementations.

The biometric sensor may be configured to generate a biometric output signal conveying information related to a biometric feature of a user. The biometric output signal may be used to identify and/or authenticate a user of the personal wellness device. A biometric feature of a user may include physiological characteristics related to the shape of the body of the user.

The pedometer may be configured to generate a step output signal that conveys information related to steps taken by a user carrying the personal wellness device. The step output signal may be used to determine a number of steps taken, a distance traveled, and/or other information related to or derived from steps taken by a user.

The electrical muscle stimulation interface may be configured to removably couple the personal wellness device with an electrode. The electrode may be configured to provide electrical muscle stimulation to a user. In some implementations, electronic pulses (or other waveforms) may be provided by the electrical muscle stimulation interface to the electrode, which in turn may deliver the electrical pulses to a surface area of a user's body causing proximate muscles to exercise passively.

The camera device may be configured to capture visual data. The visual data may include still images, video, and/or other visual data. In some implementations, the camera device may be utilized as the biometric sensor.

The actuator may be configured to provide tactile feedback to a user. Tactile feedback may be preferable in some use scenarios, for example, where other feedback mechanisms such as audio or visual may be undesired. Tactile feedback may include forces, vibrations, motions, and/or other tactile feedback provided to the user. The actuator may include a mechanical device configured to cause one or more motions of the personal wellness device.

The user interface may be configured to receive information from a user and provide information to the user. As such, the user interface may include hardware and/or software to facilitate receiving information from the user and/or providing information to the user. Examples of input devices may include one or more of a touch screen, a touch pad, a keypad, a switch, an analog stick, a button, a dial, a microphone, biometric sensor, and/or other hardware configured to receive information from a user. Examples of output devices may include one or more of a display, touch screen, speakers, and/or other hardware configured to provide information to a user. According to some implementations, the user interface may be accessible by a user with the personal wellness device in an open configuration. With the personal wellness device in a closed configuration, all, some, or none of the user interface may be accessible by a user, in various implementations.

The communications apparatus may be configured to receive information and/or transmit information from the personal wellness device. As such, the communications apparatus may include one or both of a wireless communications interface or a wired communications interface. The communications apparatus may be configured to communicatively couple the personal wellness device with a computing platform (e.g., the personal computing platform and/or the personal wellness platform server) configured to receive and process information related to compressive force exerted on the two housing bodies, a user accessory that is separate and distinct from the personal wellness device, and/or other components of the personal wellness system.

As indicated above, the personal wellness device may include a power supply, electronic storage, a processor, and/or other components. The power supply may be configured to supply electrical power to one or more components of the personal wellness device. The electronic storage may be configured to electronically store information. The processor may be configured to execute computer program modules.

The user accessory may be configured to be physically and/or communicatively coupled with the personal wellness device. The user accessory may be configured extend exercise capabilities of the personal wellness device, provide therapy to a user of the personal wellness device, facilitate monitoring of one or more vital signs of a user of the personal wellness device, and/or extend other functionalities of the personal wellness device.

The personal computing platform may include one or more of electronic storage, at least one processor, and/or other components. The electronic storage may be configured to electronically store information. The processor may be configured to execute computer program modules. The personal computing platform may be configured to communicatively couple with the personal wellness device and/or other components of the personal wellness system. According to some implementations, the computing platform may include one or more of a personal computer, a laptop computer, a tablet computer, a Smart phone, a personal digital assistant (PDA), a gaming console, and/or other personal computing platforms.

The personal wellness platform server may include one or more of electronic storage, at least one processor, and/or other components. The electronic storage may be configured to electronically store information. The processor may be configured to execute computer program modules. The personal wellness platform server may be configured to communicatively couple with the personal wellness device and/or other components of the personal wellness system.

The processor(s) of the personal wellness device, the personal computing platform, and/or the personal wellness platform server may be configured to provide information processing capabilities in the personal wellness system. One or more of these processors may be configured to execute one or more of a presentation module, a voice command module, a biometric module, an emergency alert module, a backup module, an update module, a communication module, and/or other computer program modules.

The presentation module may be configured to present, via the user interface of the personal wellness device, information associated with the personal wellness system. Such information may be presented visually, audibly, and/or other presentation manners. According to some implementations, the presentation module may be configured to present information derived from a force output signal provided by the force sensor, information derived from a location output signal provided by the geo-location sensor, information derived from a motion output signal provided by the motion sensor, information derived from a step output signal provided by the pedometer, information derived from a heart rate output signal provided by the heart rate sensor, information derived from a blood pressure output signal provided by a blood pressure sensor, information provided by one or more other modules, and/or other information associated with the personal wellness system.

The voice command module may be configured to receive voice commands and initiate corresponding operations based on the received voice commands. In some implementations where the user interface of the personal wellness device includes a microphone, the voice command module may be configured to receive audio information captured by the microphone that includes a voice command. The voice command module may be configured to initiate, responsive to reception of the audio information including the voice command, an operation by the one or more processors corresponding to the voice command in the received audio information. The voice command module may utilize one or more of speech recognition, speech to text, and/or other voice-based technologies. The voice command module may be configured to identify a speaker based on the speaker's voice.

The biometric module may be configured to identify and/or authenticate a user based on biometric information. The biometric information may be derived from a biometric output signal provided by the biometric sensor. The biometric information may be associated with a biometric feature of a user such as physiological characteristics related to the shape of the body of the user. Examples of physiological characteristics may include particular geometries of a fingerprint, face, palm, hand, iris, retina, and/or other physiological characteristics. The biometric module may identify and/or authenticate a given user by comparing biometric information associated with the given user with biometric information stored by the personal wellness device, the personal computing platform, the personal wellness platform server, and/or other components of the personal wellness system.

The emergency alert module may be configured to monitor one or more vital signs of a user associated with the personal wellness device. Examples of vital signs may include one or more of body temperature, heart rate, respiration rate, blood pressure, and/or other vital signs. Monitoring of vital signs may be performed via and/or in conjunction with a heart rate sensor, a blood pressure sensor, and/or other sensors included in or communicatively coupled with the personal wellness device. The emergency alert module may be configured to provide an emergency alert to an emergency response service responsive to individual ones of the one or more vital signs meeting a threshold condition. For example, an emergency alert may be sent to an emergency response service responsive to the heart rate of a user falling below a threshold rate.

The backup module may be configured to back up information stored by the personal wellness device. Information stored by the personal wellness device may be transmitted to a remote electronic storage configured to electronically store information. The backup module may be configured to perform a backup according to a schedule, responsive to a command received from a user, responsive to information being stored by the personal wellness device, responsive to the personal wellness device becoming communicatively coupled with the personal computing platform and/or the personal wellness platform server, and/or based on other criteria.

The update module to manage updates of software and/or firmware of the personal wellness device. Software updates and/or firmware updates may be transmitted from the personal computing platform, the personal wellness platform server, and/or other components of the personal wellness system. Software updates and/or firmware updates may be received by the personal wellness device. Software updates and/or firmware updates may be implemented on the processor and/or other components of the personal wellness device.

The communication module may be configured to provide interpersonal communications capabilities to the personal wellness device. Examples of interpersonal communications capabilities may include one or more of voice over internet protocol (VoIP), short message service (SMS), multimedia messaging service (MMS), video conferencing, telephony, and/or other interpersonal communication capabilities. The communication module may operate in conjunction with the user interface of the personal wellness device to provide the interpersonal communications capabilities.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION

Figure 1:
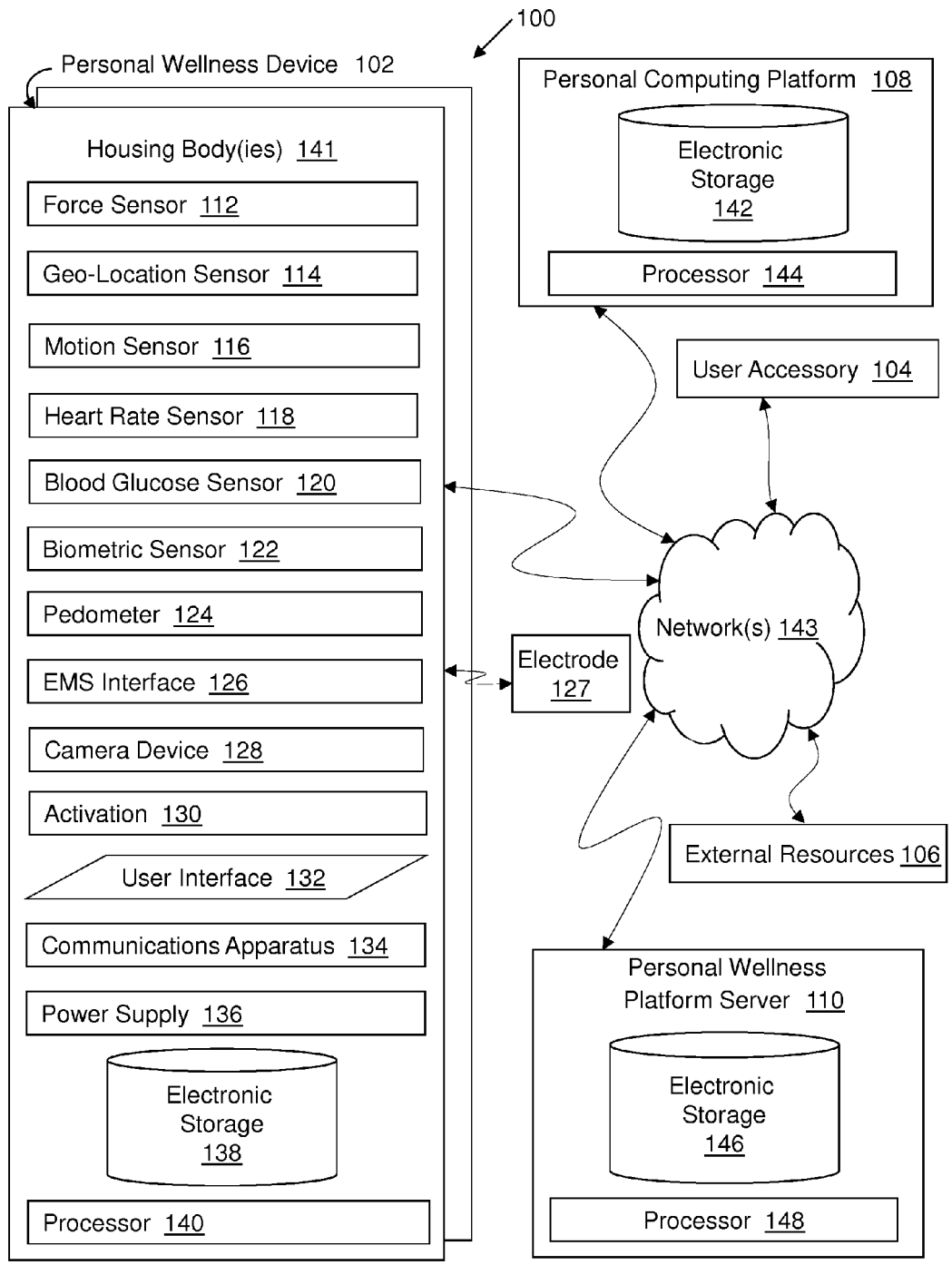
FIG. 1 illustrates a personal wellness system configured to facilitate personal wellness via a personal wellness device, in accordance with one or more implementations.

FIG. 1 illustrates a personal wellness system 100 configured to facilitate personal wellness via a personal wellness device 102, in accordance with one or more implementations. The personal wellness device 102 may be a portable, hand-held device configured to facilitate personal exercise using the device. In some implementations, compressive forces exerted on personal wellness device 102 may be measured and/or recorded through the use of a force sensor included in personal wellness device 102. Geo-location and/or motion of personal wellness device 102 may be utilized in measuring and/or recording personal exercises performed with personal wellness device 102. Steps taken and/or distance traveled may be determined, in some implementations, by use of a pedometer included in personal wellness device 102. Therapy such as electrical muscle stimulation (EMS) may be facilitated by personal wellness device 102.

The personal wellness device 102 may promote personal wellness by determining and/or evaluating aspects of personal health and/or exercise. By way of non-limiting example, aspects of personal health may include vital signs, trends in personal fitness, frequency of exercise, and/or other aspects of personal health, while aspects of personal exercise may include number of repetitions, calories burnt, duration of exercise, and/or other aspects of personal exercise. In some implementation, the personal wellness device 102 may facilitate personal wellness management, as described in U.S. patent application Ser. No. 13/527,401, filed on Jun. 19, 2012, and entitled "Personal Wellness Management Platform," which is incorporated herein by reference.

The personal wellness device 102 may be configured to facilitate interpersonal communications, such as voice over internet protocol, short message service, multimedia messaging service, video conferencing, telephony, and/or other interpersonal communications. The personal wellness device 102 may facilitate socializing and/or merchandizing, according to some implementations, as described in U.S. patent application Ser. No. 13/527,437, filed on Jun. 19, 2012, and entitled "Merchandizing, Socializing, and/or Gaming Via a Personal Wellness Device and/or a Personal Wellness Platform," which is incorporated herein by reference.

In addition to personal wellness device 102, personal wellness system 100 may include one or more of a user accessory 104, external resources 106, a personal computing platform 108, a personal wellness platform server 110, and/or other components, which may complement and/or include one or more functionalities attributed herein to personal wellness device 102. Components of personal wellness system 100, such as personal wellness device 102, personal computing platform 108, personal wellness platform server 110, user accessory 104, and/or external resources 106, may be operatively linked via one or more electronic communication links. For example, such electronic communication links may be established, at least in part, via wired or wireless network(s) 143, which may include the Internet, WiFi, LAN, Bluetooth, and/or other networks. It will be appreciated that this is not intended to be limiting, and that the scope of this disclosure includes implementations in which personal wellness device 102, personal computing platform 108, personal wellness platform server 110, user accessory 104, and/or external resources 106 are operatively linked via some other communication media.

As depicted in FIG. 1, personal wellness device 102 may include one or more of a force sensor 112, a geo-location sensor 114, a motion sensor 116, a heart rate sensor 118, a blood glucose sensor 120, a biometric sensor 122, a pedometer 124, an electrical muscle stimulation (EMS) interface 126, a camera device 128, an actuator 130, a user interface 132, communications apparatus 134, a power supply 136, electronic storage 138, a processor 140, and/or other components. One or more components of personal wellness device 102 may be housed by one or more housing bodies, as described in connection with FIGS. 2A, 2B, 3A, 3B, 3C, 3D, 4A, and 4B. In implementations having two housing bodies, a first housing body and a second housing body may be movably coupled together by way of a coupling mechanism such that the two housing bodies are reconfigurable between an open configuration and a closed configuration. The two housing bodies may be configured to receive compressive force during personal exercise while in the closed configuration.

The force sensor 112 may be configured to generate a force output signal that conveys information related to compressive force exerted on personal wellness device 102. Such information may include or be used to determine magnitude of force, duration of force, a force magnitude profile as a function of time, a quantity of compressive forces, and/or other information related to compressive force exerted on personal wellness device 102. The force output signal generated by force sensor 112 may be received and/or utilized by one or more modules executable by processor 140, as described further herein. By way of non-limiting example, force sensor 112 may include a FlexiForce A201 force sensor from Tekscan. However, other apparatus configured for force sensing are contemplated and within the scope of the invention.

The geo-location sensor 114 may be configured to generate a location output signal conveying information related to a geo-location of personal wellness device 102. The location output signal may be used to quantify one or more parameters of personal exercise. Such parameters may include speed, distance traveled, course of travel, and/or other parameters related to a geo-location of personal wellness device 102. By way of non-limiting example, geo-location sensor 114 may include a GPS device and/or other device configured to generate signals related to geo-location. However, other apparatus and techniques for location sensing and/or detecting are contemplated and within the scope of the invention.

The motion sensor 116 may be configured to generate a motion output signal that conveys information related to a motion and/or orientation of personal wellness device 102. The motion output signal may be used to quantify motions, changes in motion, orientation, changes in orientation, and/or information derived therefrom. By way of non-limiting example, motion sensor 116 may include an accelerometer configured to generate signals related to motion and/or orientation. However, other apparatus and techniques for motion and/or orientation sensing and/or detection are contemplated and within the scope of the invention.

The heart rate sensor 118 may be configured to generate a heart rate output signal that conveys information related to a heart rate of a user associated with personal wellness device 102. The heart rate sensor 118 may utilize electrocardiography (ECG or EKG). The heart rate output signal may be used to monitor heart rate in real time or record heart rate data for later observation and/or analysis. In some implementations, heart rate sensor 118 is integrated into personal wellness device 102 such that heart rate sensor 118 may measure a user's heart rate by way of physical contact between the user and personal wellness device 102. The heart rate sensor 118 may communicatively couple with a heart rate monitor that is separate and distinct from personal wellness device 102, according to some implementations. Examples of separate and distinct heart rate monitors may include a chest strap, a finger clip, a garment with an integrated heart rate monitor, and/or other devices configured to probe heart rate.

The blood glucose sensor 120 may be configured to generate a glucose output signal that conveys information related to a concentration of glucose in the blood of a user associated with personal wellness device 102. The glucose output signal may be used to determine a concentration of glucose and/or information derived therefrom. In some implementations, blood glucose sensor 120 may require a blood sample from a user in order to generate the glucose output signal. The blood glucose sensor 120 may be based on one or more non-invasive technologies including near IR detection, ultrasound, dielectric spectroscopy, and/or other non-invasive technologies for determining glucose concentration, in accordance with some implementations.

The biometric sensor 122 may be configured to generate a biometric output signal conveying information related to a biometric feature of a user. The biometric output signal may be used to identify and/or authenticate a user of personal wellness device 102. A biometric feature of a user may include physiological characteristics related to the shape of the body of the user. Examples of physiological characteristics may include particular geometries of a fingerprint, face, palm, hand, iris, retina, and/or other physiological characteristics. The biometric sensor 122 may include an image capture device, a biometric scanner, and/or other device configured to observe biometric features. In some implementations, biometric sensor 122 is included in user interface 132.

The pedometer 124 may be configured to generate a step output signal that conveys information related to steps taken by a user carrying personal wellness device 102. The step output signal may be used to determine a number of steps taken, a distance traveled, and/or other information related to or derived from steps taken by a user. In some implementations, pedometer 124 may include a separate and distinct device communicatively coupled with personal wellness device 102 and configured to transmit the step output signal to personal wellness device 102.

The electrical muscle stimulation interface 126 may be configured to removably couple personal wellness device 102 with an electrode 127. The electrode 127 may be configured to provide electrical muscle stimulation to a user. In some implementations, electronic pulses (or other waveforms) may be provided by electrical muscle stimulation interface 126 to electrode 127, which in turn may deliver the electrical pulses to a surface area of a user's body causing proximate muscles to exercise passively.

The camera device 128 may be configured to capture visual data. The visual data may include still images, video, and/or other visual data. In some implementations, camera device 128 may be utilized as biometric sensor 122. The camera device 128 may include, by way of non-limiting example, a digital camera and/or other imaging devices.

The actuator 130 may be configured to provide tactile feedback to a user. Tactile feedback may be preferable in some use scenarios, for example, where other feedback mechanisms such as audio or visual may be undesired. Tactile feedback may include forces, vibrations, motions, and/or other tactile feedback provided to the user. The actuator 130 may include a mechanical device configured to cause one or more motions of personal wellness device 102. In some implementations, actuator 130 may include an electric motor with an unbalanced mass on its driveshaft such that rotation of the driveshaft generates vibrations. One or more parameters of the tactile feedback may be varied to convey different information to a user. The parameters may include one or more of direction, source location, duration, frequency, amplitude, and/or other parameters.

The user interface 132 may be configured to receive information from a user and provide information to the user. As such, user interface 132 may include hardware and/or software to facilitate receiving information from the user and/or providing information to the user. Examples of input devices may include one or more of a touch screen, a touch pad, a keypad, a switch, an analog stick, a button, a dial, a microphone, biometric sensor, and/or other hardware configured to receive information from a user. Examples of output devices may include one or more of a display, touch screen, speakers, and/or other hardware configured to provide information to a user.

According to some implementations, user interface 132 may be accessible by a user with personal wellness device 102 in an open configuration, as described in connection with FIGS. 2A, 2B, 3A, 3B, 3C, 3D, 4A, and/or 4B. With personal wellness device 102 in a closed configuration, all, some, or none of user interface 132 may be accessible by a user, in various implementations.

In some implementations, user interface 132 may be configured to present user configurable settings to the user. The user interface 132 may be configured to receive selections from the user of values for the user configurable settings. One or more user configurable settings may impact the current activity of one or more components of personal wellness device 102. By way of non-limiting example, the user configurable settings may activate and/or deactivate one or more components of personal wellness device 102, and/or may configure one or more aspects of operation of personal wellness device 102. The user configurable settings may be related to personal exercise and/or wellness of a user of personal wellness device 102. The user configurable settings may be provided to processor 140 of personal wellness device 102. The user configurable settings may be provided to one or more processors of user accessory 104, personal computing platform 108, personal wellness platform server 110, and/or other components of personal wellness system 100.

The communications apparatus 134 may be configured to receive information and/or transmit information from personal wellness device 102. As such, communications apparatus 134 may include one or both of a wireless communications interface or a wired communications interface. Examples of a communications interface may include a wired or wireless transmitter, a wired or wireless receiver, and/or a combined wired or wireless transmitter and receiver. The communications apparatus 134 may be configured to communicatively couple personal wellness device 102 with a computing platform (e.g., personal computing platform 108 and/or personal wellness platform server 110) configured to receive and process information related to compressive force exerted on the two housing bodies, a user accessory that is separate and distinct from personal wellness device 102, and/or other components of personal wellness system 100.

The power supply 136 may be configured to supply electrical power to one or more components of personal wellness device 102. By way of non-limiting example, power supply 136 may include one or more of a battery, a capacitor, apparatus for receiving electrical power from an external source (e.g., a wall socket), and/or other power supplies. In some implementations, power supply 136 may be rechargeable. In one implementation, where communications apparatus 134 includes a USB port or other wired communications port, communications apparatus 134 may receive electrical power from a component of personal wellness system 100 and/or another source to recharge power supply 136.

The electronic storage 138 may be configured to electronically store information. Exemplary implementations of electronic storage that is the same or similar to electronic storage 138 are described further herein.

The processor 140 may be configured to execute computer program modules. Exemplary implementations of processors that are the same or similar to processor 140 are described in connection with FIG. 5.

FIGS. 2A, 2B, 3A, 3B, 3C, 3D, 4A, and 4B illustrate exemplary open and/or closed configurations of various implementations of personal wellness device 102. Generally speaking, these implementations may include two housing bodies: a first housing body and a second housing body. The first housing body and the second housing body may be movably coupled together by way of a coupling mechanism such that the two housing bodies are reconfigurable between an open configuration and a closed configuration. The coupling mechanism may include one or more of a hinge, a joint, a swivel, a sliding track, and/or other coupling mechanism configured to movably couple two bodies. The two housing bodies may be configured to receive compressive force during personal exercise while in the closed configuration.

One or more housing bodies of personal wellness device 102 may be configured to house and/or carry one or more other components of personal wellness device 102. These one or more other components may be disposed partially or wholly within a housing body, or be affixed to an external surface of the housing body. In some implementations, a housing body includes a flexible, yet resilient, material such as, for example, flexible, hard rubber.

According to some implementations, two housing bodies may be fully separated and docked together, either next to each other or one fully or partially enclosed into the other. In such implementations, one body may include a pressure sensor and/or other components configured for various measuring capabilities, while the other body may include a user interface. The two separate housing bodies may communicate wirelessly with each other when separated. When docked, the two separate housing bodies may communicate wirelessly and/or via a docking port, which may also be used for charging one housing body from the other housing body. Such implementations may enabling the user interface to be accessible during exercising.

Figure 2A:
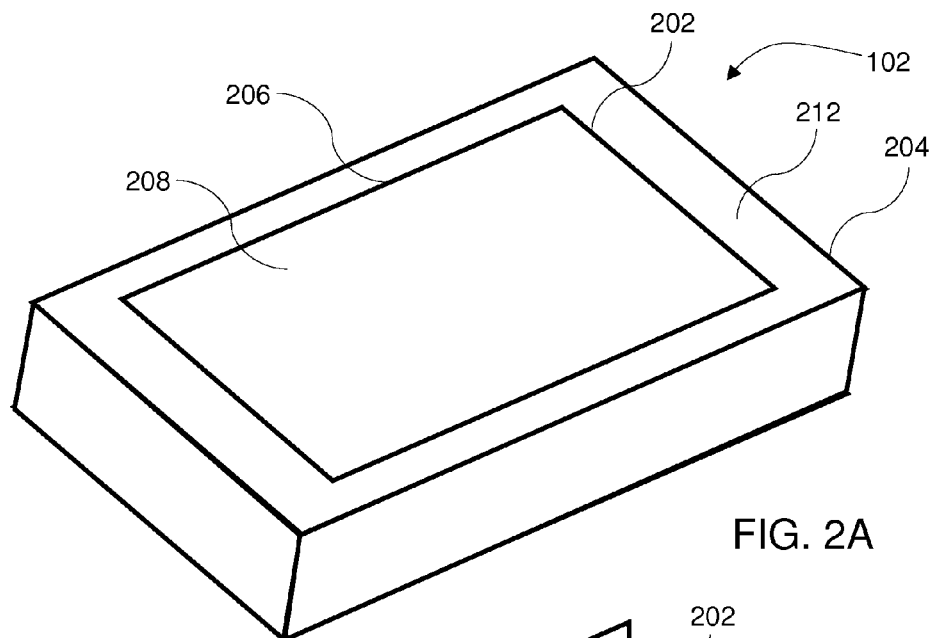
FIGS. 2A, 2B, 3A, 3B, 3C, 3D, 4A, and 4B illustrate exemplary open and/or closed configurations of various implementations of a personal wellness device.
Figure 2B:
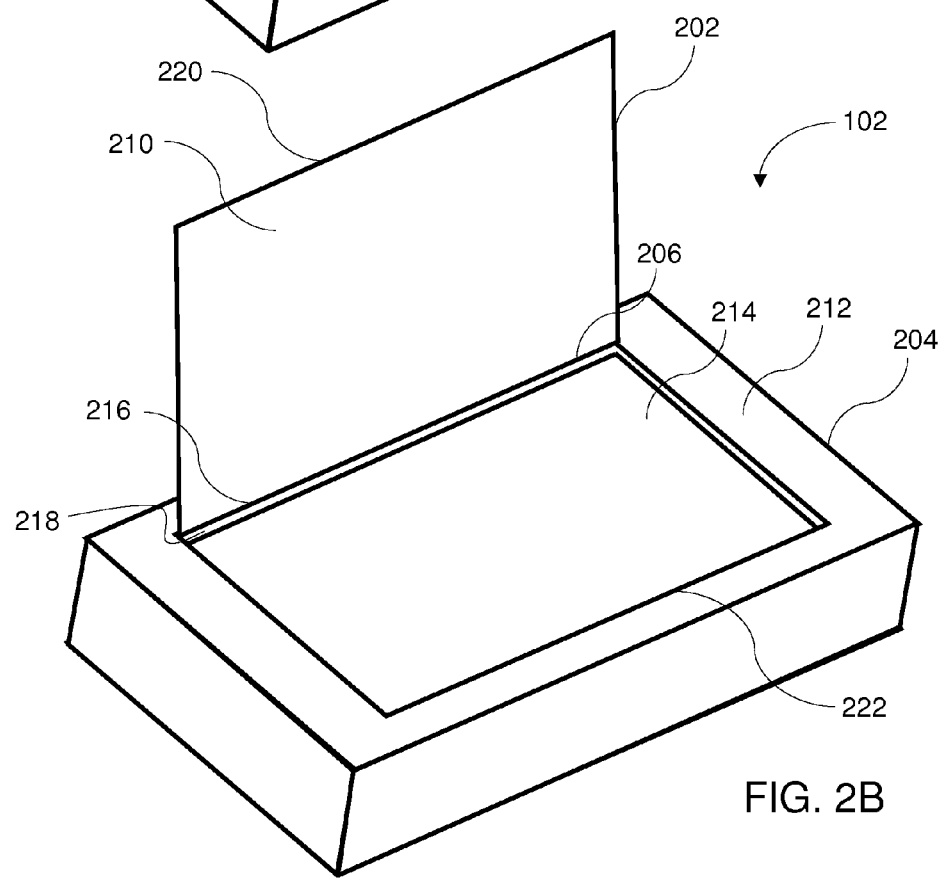

FIGS. 2A and 2B illustrate, respectively, exemplary closed and open configurations of an implementation of personal wellness device 102 having a first housing body 202 and a second housing body 204 movably coupled together by coupling mechanism 206. The first housing body 202 may include an obverse side 208 and a reverse side 210. The second housing body 204 may include a top side 212 and a bottom side (not visible in FIGS. 2A and 2B). The top side 212 may include a recess 214. The coupling mechanism 206 may be configured to movably couple a proximal edge 216 of first housing body 202 with a proximal edge 218 of recess 214. By way of non-limiting example, coupling mechanism 206 may include a hinge, hinging mechanism, and/or other mechanism configured movably couple first housing body 202 and second housing body 204. A distal edge 220 of first housing body 202 may swing toward or away from a distal edge 222 of recess 214 about an axis of rotation formed by coupling mechanism 206. A user interface that is the same or similar to user interface 132 may be wholly or partially located in recess 214 and/or on reverse side 210 of first housing body 202. As such, a user may access some or all of the user interface located in recess 214 and/or on reverse side 210 with personal wellness device 102 in the open configuration (see FIG. 2B). In the closed configuration (see FIG. 2A), first housing body 202 may fit wholly or partially within recess 214. A force sensor that is the same or similar to force sensor 112 may be disposed proximate to obverse side 208 of first housing body 202 and/or the bottom side of second housing body 204. During exercise, with personal wellness device 102 in the closed configuration, a compressive force may be applied in opposing directions substantially normal to obverse side 208 of first housing body 202 and the bottom side of second housing body 204.

Figure 3A:
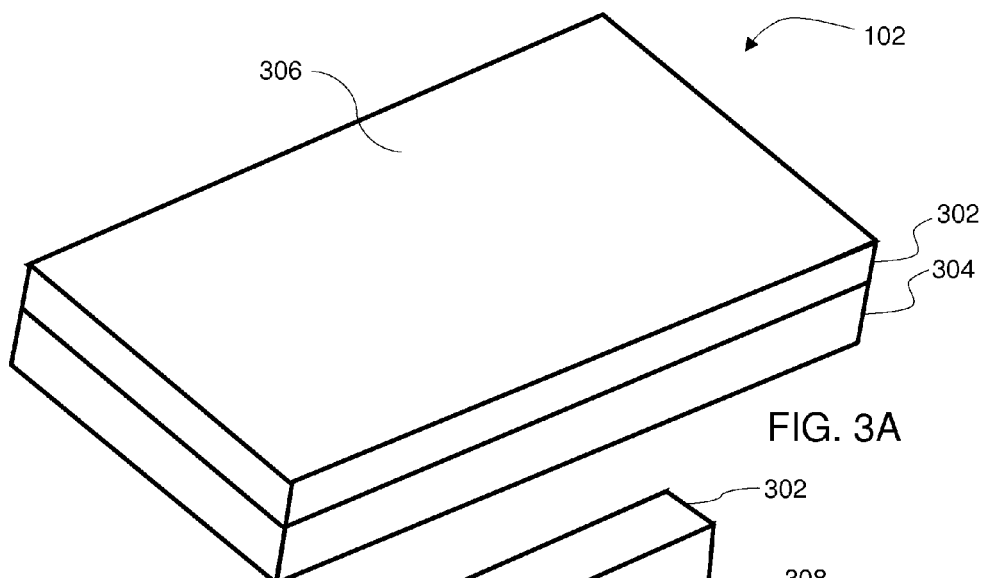
Figure 3B:
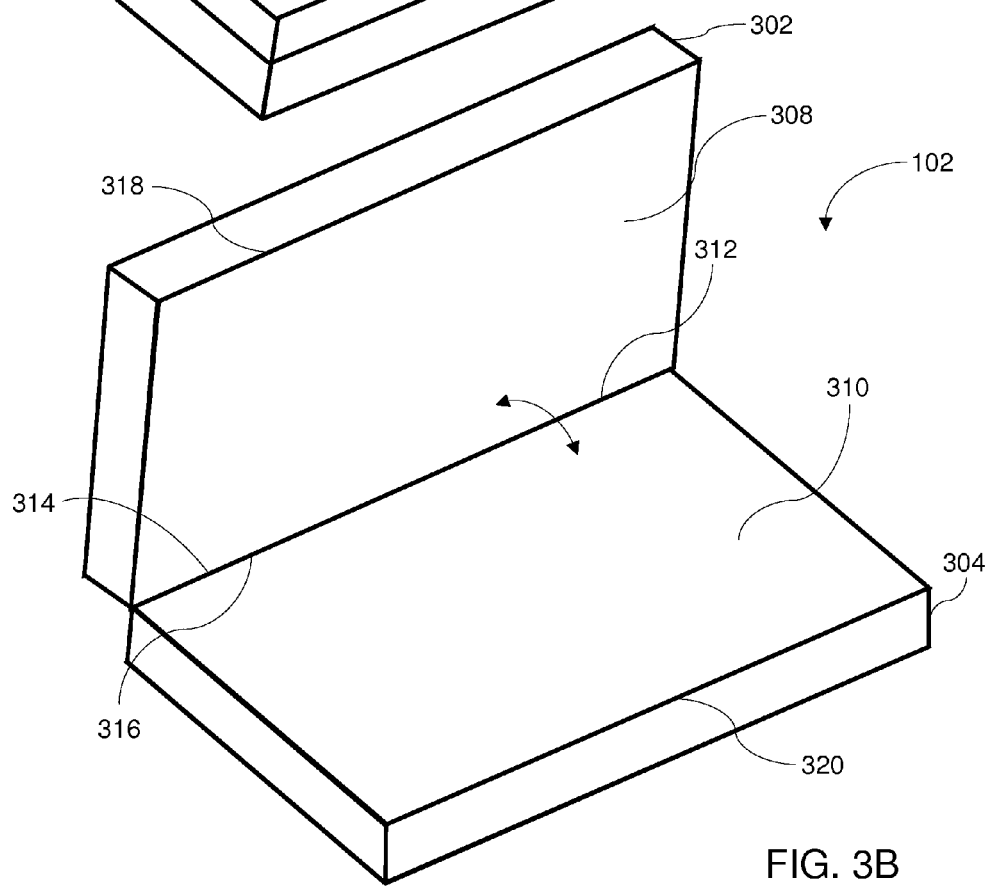
Figure 3C:
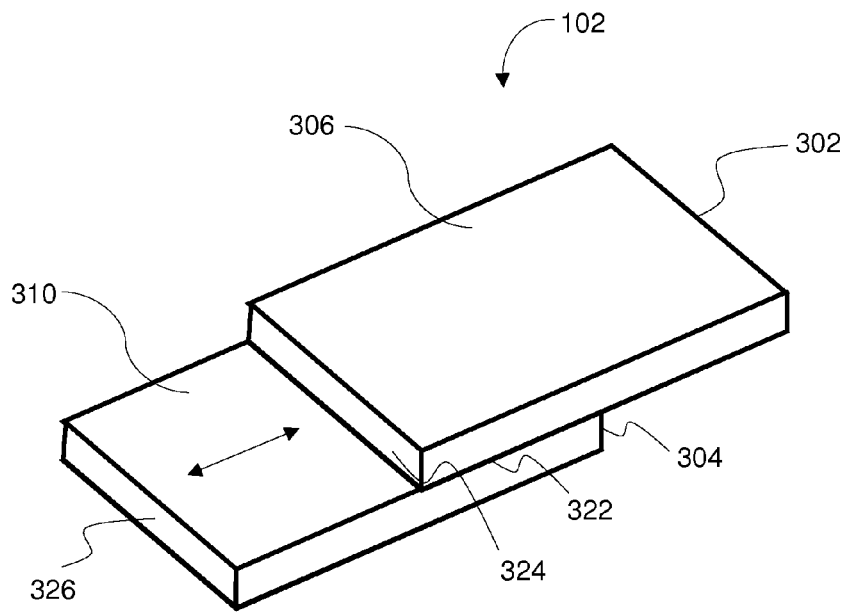
Figure 3D:
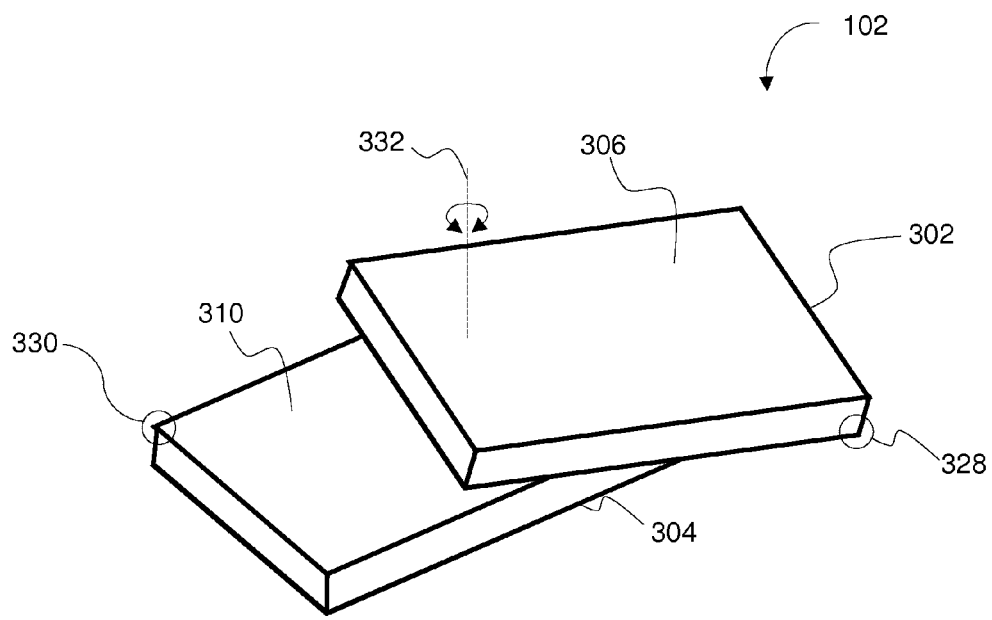

FIG. 3A illustrates an exemplary closed configuration while FIGS. 3B, 3C, and 3D illustrate exemplary open configurations of implementations of personal wellness device 102 having a first housing body 302 and a second housing body 304 movably coupled together by various coupling mechanisms. The first housing body 302 may include an external face 306 and an internal face 308 (not visible in FIGS. 3A, 3C, and 3D). The second housing body 304 may include an external face (not visible in FIGS. 3A, 3B, 3C, and 3D) and an internal face 310. In the closed configuration (see FIG. 3A), internal face 308 of first housing body 302 and internal face 310 of second housing body 304 may be concealed and/or inaccessible by a user. A user interface that is the same or similar to user interface 132 may be wholly or partially disposed at internal face 308 of first housing body 302 and/or internal face 310 of second housing body 304. As such, a user may access some or all of the user interface with personal wellness device 102 in the open configuration (see FIGS. 3B, 3C, and 3D). A force sensor that is the same or similar to force sensor 112 may be disposed proximate to external face 306 of first housing body 302 and/or the external face of second housing body 304. During exercise, with personal wellness device 102 in the closed configuration, a compressive force may be applied in opposing directions substantially normal to external face 306 of first housing body 302 and the external face of second housing body 304.

In the implementation illustrated in FIG. 3B, first housing body 302 and second housing body 304 may be movably coupled together by way of coupling mechanism 312. The coupling mechanism 312 may be configured to movably couple a proximal edge 314 of internal face 308 of first housing body 302 with a proximal edge 316 of internal face 310 of second housing body 304. By way of non-limiting example, coupling mechanism 312 may include a hinge, hinging mechanism, and/or other mechanism configured to movably couple first housing body 302 and second housing body 304. A distal edge 318 of internal face 308 of first housing body 302 may swing toward or away from a distal edge 320 of internal face 310 of second housing body 304 about an axis of rotation formed by coupling mechanism 312.

In the implementation illustrated in FIG. 3C, first housing body 302 and second housing body 304 may be movably coupled together by way of coupling mechanism 322. The coupling mechanism 322 may be configured to movably couple a portion of internal face 308 (not visible in FIG. 3C) of first housing body 302 with a portion of internal face 310 of second housing body 304. By way of non-limiting example, coupling mechanism 322 may include a track, a slide, and/or other mechanism configured to provide linear translation between first housing body 302 and second housing body 304 while being movably coupled together. A first end face 324 of first housing body 302 may slide toward or away from a second end face 326 of second housing body 304, as guided by coupling mechanism 322.

In the implementation illustrated in FIG. 3D, first housing body 302 and second housing body 304 may be movably coupled together by way of a pivot coupling mechanism (not visible in FIG. 3D). The pivot coupling mechanism may be configured to movably couple internal face 308 of first housing body 302 with internal face 310 of second housing body 304 such that first housing body 302 and second housing body 304 may pivot or rotate relative to each other. By way of non-limiting example, the pivot coupling mechanism may include a pivot, swivel, joint, and/or other mechanism configured to provide rotation between first housing body 302 and second housing body 304 while being movably coupled together. A first corner 328 of first housing body 302 may rotate toward or away from a second corner 330 of second housing body 304 about an axis of rotation 332 formed by the pivot coupling mechanism.

Figure 4A:
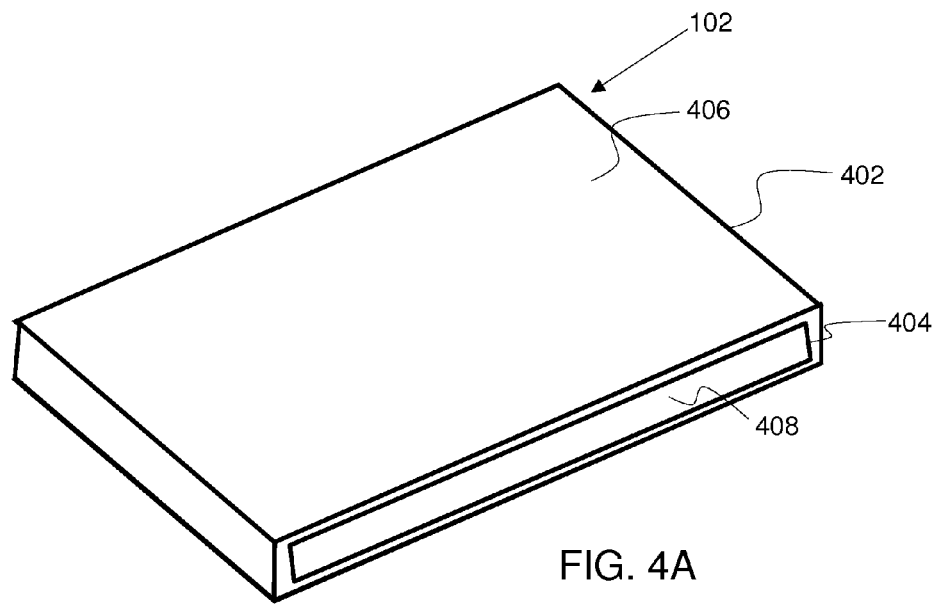
Figure 4B:
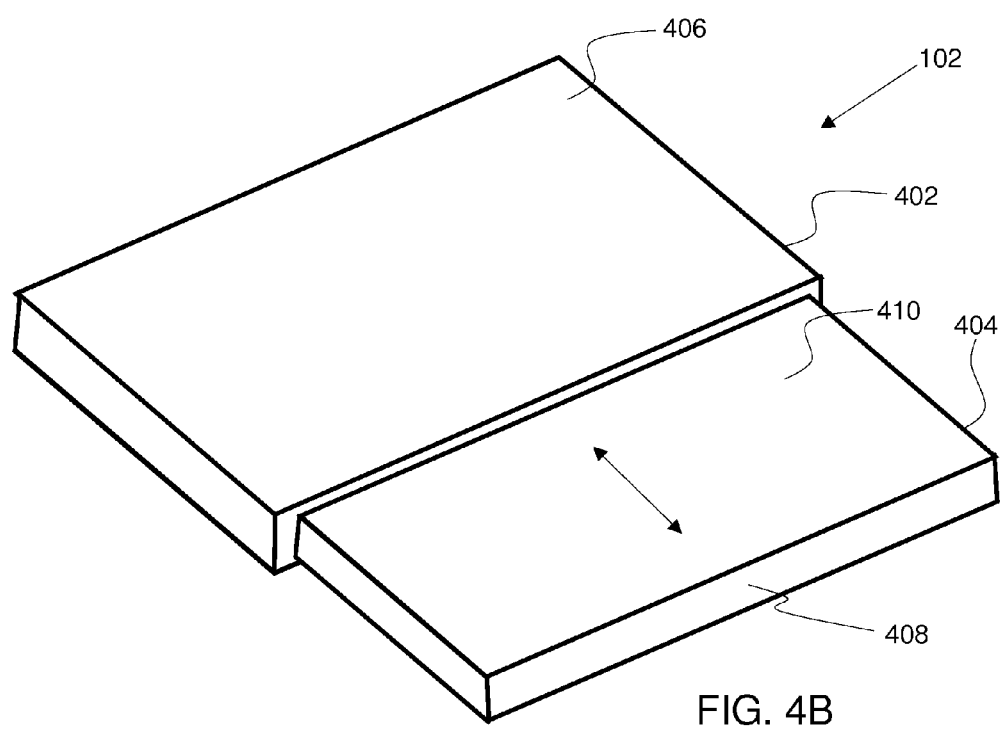

FIGS. 4A and 4B illustrate, respectively, exemplary closed and open configurations of an implementation of personal wellness device 102 having a first housing body 402 and a second housing body 404 movably coupled together by a sliding coupling mechanism (not visible in FIGS. 4A and 4B). The first housing body 402 may include a top external face 406 and a bottom external face (not visible in FIGS. 4A and 4B). The second housing body 304 may include an external end face 408, a top internal face 410, and a bottom internal face (not visible in FIGS. 4A and 4B). By way of non-limiting example, the sliding coupling mechanism may include a track, a slide, and/or other mechanism configured to provide linear translation between first housing body 402 and second housing body 404 while being movably coupled together. The external end face 408 of second housing body 404 may slide toward or away from first housing body 402, as guided by the sliding coupling mechanism. In the closed configuration (see FIG. 4A), first housing body 402 may completely encase second housing body 404 except for external end face 408, which may remain exposed. A user interface that is the same or similar to user interface 132 may be wholly or partially located on top internal face 410 and/or the bottom internal face of second housing body 404. As such, a user may access some or all of the user interface located top internal face 410 and/or the bottom internal face of second housing body 404 with personal wellness device 102 in the open configuration (see FIG. 4B). A force sensor that is the same or similar to force sensor 112 may be disposed proximate to top external face 406 and/or the bottom external face of first housing body 402. During exercise, with personal wellness device 102 in the closed configuration, a compressive force may be applied in opposing directions substantially normal to top external face 406 and the bottom external face of first housing body 402.

While several configurations of personal wellness device 102 are described in connection with FIGS. 2A, 2B, 3A, 3B, 3C, 3D, 4A, and 4B, this is not intended to be limiting as other configurations are contemplated and fall within the scope of the invention.

Turning back to FIG. 1, the user accessory 104 may be configured to be physically and/or communicatively coupled with personal wellness device 102. The user accessory 104 may be configured extend exercise capabilities of personal wellness device 102, provide therapy to a user of personal wellness device 102, facilitate monitoring of one or more vital signs of a user of personal wellness device 102, extend gaming capabilities of personal wellness device 102, and/or extend other functionalities of personal wellness device 102.

In implementations where user accessory 104 is configured to extend exercise capabilities of personal wellness device 102, user accessory 104 may include a strap (not depicted in FIG. 1) or other apparatus configured for similar functionality attributed herein to the strap. Such a strap may be configured to physically couple to personal wellness device 102 and facilitate exertion of compressive force on personal wellness device 102 responsive to a tensive force exerted on the strap. The strap may be removably coupled to personal wellness device 102 by hooks, snaps, hook and loop fasteners, and/or other means for removable coupling.

In implementations where user accessory 104 is configured to provide therapy to a user of personal wellness device 102, user accessory 104 may include electrode 127. In some implementations, electrical muscle stimulation interface 126 may be configured to removably couple personal wellness device 102 with electrode 127. The electrode 127 may be configured to provide electrical muscle stimulation to a user.

In implementations where user accessory 104 is configured to facilitate monitoring of one or more vital signs of a user of personal wellness device 102, user accessory 104 may include one or more accessories configured to facilitate monitoring of one or more of body temperature, heart rate, respiration rate, blood pressure, body sweat, and/or other vital signs. In some implementations, user accessory 104 may include a chest strap, a finger clip, a garment with an integrated heart rate monitor, and/or other devices configured to probe heart rate, which may communicatively couple with heart rate sensor 118. In some implementations, user accessory 104 may include a blood pressure sensor. The blood pressure sensor may be configured to generate a blood pressure output signal that conveys information related to a blood pressure of a user associated with personal wellness device 102.

In implementations where user accessory 104 is configured to extend other functionalities of personal wellness device 102, user accessory 104 may include one or more of a wired headset; a wireless headset; wired headphones; wireless headphones; a device that includes a display; one or more sensors configured to be attached to a user's body and provide a signal conveying information associated with motion, position, and/or other information associated with a user; a device configured to determine user and/or body part motion, size, and/or position (e.g., MS Kinect™); and/or other accessories configured to extend one or more functionalities of personal wellness device 102. A device configured to determine user and/or body part motion, size, and/or position may perform such determination(s) based on optical information, signals received from one or more sensors attached to a user's body, and/or other information associated with user.

The external resources 106 may include sources of information, hosts and/or providers of personal wellness systems, external entities participating with personal wellness system 100, and/or other resources. In some implementations, some or all of the functionality attributed herein to external resources 106 may be provided by resources included in personal wellness system 100.

The personal computing platform 108 may include one or more of electronic storage 142, at least one processor 144, and/or other components. The electronic storage 142 may be configured to electronically store information. Exemplary implementations of electronic storage that is the same or similar to electronic storage 142 are described further herein. The processor 144 may be configured to execute computer program modules. Exemplary implementations of processors that are the same or similar to processor 144 are described in connection with FIG. 5. The personal computing platform 108 may be configured to communicatively couple with personal wellness device 102 and/or other components of personal wellness system 100. The personal computing platform 108 may be configured to receive, transmit, process, and/or store information related to one or more of personal exercise, compressive force exerted on personal wellness device 102, and/or other information associated with personal wellness system 100. According to some implementations, the computing platform 104 may include one or more of a personal computer, a laptop computer, a tablet computer, a Smart phone, a personal digital assistant (PDA), a gaming console, and/or other personal computing platforms.

The personal wellness platform server 110 may include one or more of electronic storage 146, at least one processor 148, and/or other components. The electronic storage 146 may be configured to electronically store information. Exemplary implementations of electronic storage that is the same or similar to electronic storage 146 are described further herein. The processor 148 may be configured to execute computer program modules. Exemplary implementations of processors that are the same or similar to processor 146 are described in connection with FIG. 5. The personal wellness platform server 110 may be configured to communicatively couple with personal wellness device 102 and/or other components of personal wellness system 100. The personal wellness platform server 110 may be configured to receive, transmit, process, and/or store information related to one or more of personal exercise, compressive force exerted on personal wellness device 102, and/or other information associated with personal wellness system 100. In some implementations, personal wellness platform server 110 may be implemented by a cloud of computing platforms operating together as personal wellness platform server 110.

Electronic storage 138 of personal wellness device 102, electronic storage 142 of personal computing platform 108, and/or electronic storage 146 of personal wellness platform server 110 may comprise electronic storage media that electronically stores information. Such electronic storage media may include one or both of system storage that is provided integrally (i.e., substantially non-removable) with personal wellness device 102, personal computing platform 108, and/ or personal wellness platform server 110. Electronic storage media may include removable storage that is removably connectable to personal wellness device 102, personal computing platform 108, and/or personal wellness platform server 110 via, for example, a port (e.g., a USB port, a firewire port, etc.)

or a drive (e.g., a disk drive, etc.). Electronic storage 138, electronic storage 142, and/or electronic storage 146 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 138, electronic storage 142, and/or electronic storage 146 may include one or more virtual storage resources (e.g., cloud storage, a virtual private network, and/or other virtual storage resources). Electronic storage 138, electronic storage 142, and/or electronic storage 146 may store software algorithms; information determined by one or more processors (e.g., processor 140, processor 144, and/or processor 148); information received from personal wellness device 102, user accessory 104, external resources 106, personal computing platform 108, and/or personal wellness platform server 110; and/or other information that enables personal wellness system 100 to function as described herein.

Figure 5:
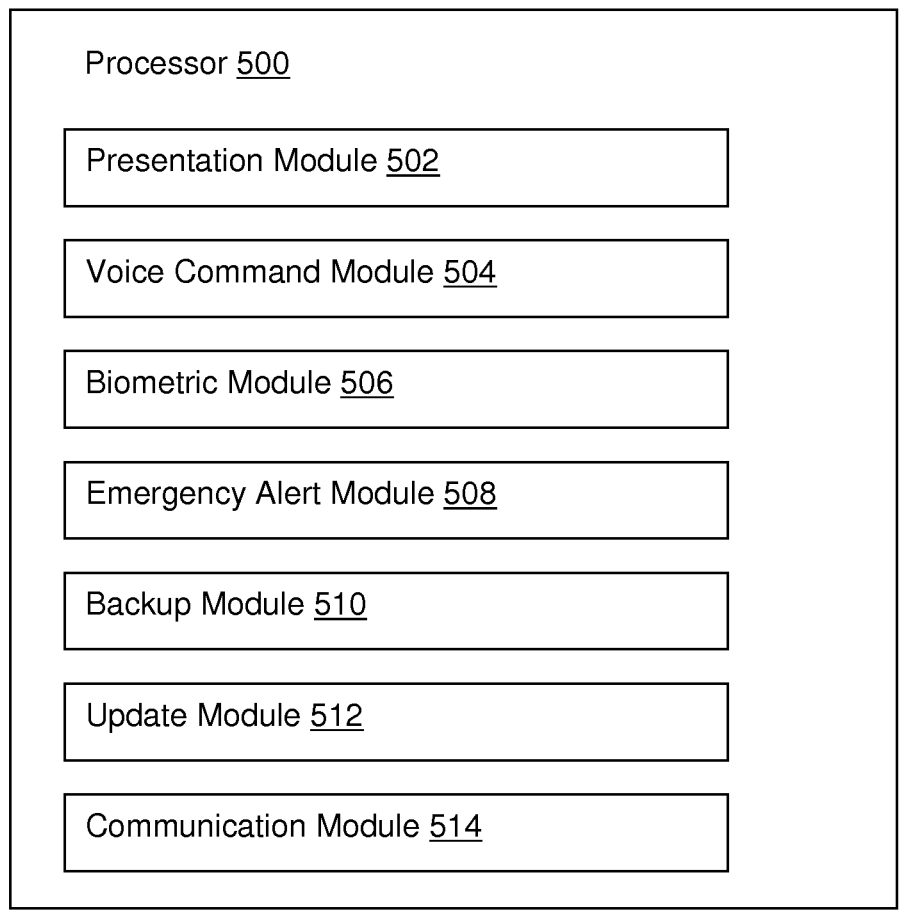
FIG. 5 illustrates an exemplary processor included in one or more components of the personal wellness system, in accordance with one or more implementations.

FIG. 5 illustrates an exemplary processor 500 included in one or more components of personal wellness system 100, in accordance with one or more implementations. The processor 500 may be the same or similar to processor 140 of personal wellness device 102, processor 144 of personal computing platform 108, and/or processor 148 of personal wellness platform server 110. Processor 500 is configured to provide information processing capabilities in personal wellness system 100. As such, processor 500 may include one or more of a digital processor, an analog processor, a digital circuit designed to process information, an analog circuit designed to process information, a state machine, and/or other mechanisms for electronically processing information. Although processor 500 is shown in FIG. 5 as a single entity, this is for illustrative purposes only. In some implementations, processor 500 may include a plurality of processing units. These processing units may be physically located within the same device, or processor 500 may represent processing functionality of a plurality of devices operating in coordination.

As depicted in FIG. 5, processor 500 may be configured to execute one or more of a presentation module 502, a voice command module 504, a biometric module 506, an emergency alert module 508, a backup module 510, an update module 512, a communication module 514, and/or other computer program modules. Processor 500 may be configured to execute modules 502, 504, 506, 508, 510, 512, 514, and/or other modules by software; hardware; firmware; some combination of software, hardware, and/or firmware; and/or other mechanisms for configuring processing capabilities on processor 500.

It should be appreciated that although modules 502, 504, 506, 508, 510, 512, and 514 are illustrated in FIG. 5 as being co-located within a single processing unit, in implementations in which processor 500 includes multiple processing units, one or more of modules 502, 504, 506, 508, 510, 512, and/or 514 may be located remotely from the other modules. For example, one or more of modules 502, 504, 506, 508, 510, 512, 514, and/or other modules may be executed by processor 140 of personal wellness device 102, processor 144 of personal computing platform 108, and/or processor 148 of personal wellness platform server 110. The description of the functionality provided by the different modules 502, 504, 506, 508, 510, 512, and/or 514 described below is for illustrative purposes, and is not intended to be limiting, as any of modules 502, 504, 506, 508, 510, 512, and/or 514 may provide more or less functionality than is described. For example, one or more of modules 502, 504, 506, 508, 510, 512, and/or 514 may be eliminated, and some or all of its functionality may be provided by other ones of modules 502, 504, 506, 508, 510, 512, and/or 514. As another example, processor 500 may be configured to execute one or more additional modules that may perform some or all of the functionality attributed below to one of modules 502, 504, 506, 508, 510, 512, and/or 514.

The presentation module 502 may be configured to present, via user interface 132, information associated with personal wellness system 100. Such information may be presented visually, audibly, and/or other presentation manners. According to some implementations, presentation module 502 may be configured to present information derived from a force output signal provided by force sensor 112, information derived from a location output signal provided by geo-location sensor 114, information derived from a motion output signal provided by motion sensor 116, information derived from a step output signal provided by pedometer 124, information derived from a heart rate output signal provided by heart rate sensor 118, information derived from a blood pressure output signal provided by a blood pressure sensor, information provided by one or more other modules, and/or other information associated with personal wellness system 100.

The voice command module 504 may be configured to receive voice commands and initiate corresponding operations based on the received voice commands. In some implementations where user interface 132 of personal wellness device 102 includes a microphone, voice command module 504 may be configured to receive audio information captured by the microphone that includes a voice command. The voice command module 504 may be configured to initiate, responsive to reception of the audio information including the voice command, an operation by the one or more processors (e.g., processor 500) corresponding to the voice command in the received audio information. The voice command module 504 may utilize one or more of speech recognition, speech to text, and/or other voice-based technologies. The voice command module 504 may be configured to identify a speaker based on the speaker's voice.

The biometric module 506 may be configured to identify and/or authenticate a user based on biometric information. The biometric information may be derived from a biometric output signal provided by biometric sensor 122. The biometric information may be associated with a biometric feature of a user such as physiological characteristics related to the shape of the body of the user. Examples of physiological characteristics may include particular geometries of a fingerprint, face, palm, hand, iris, retina, and/or other physiological characteristics. The biometric module 506 may identify and/or authenticate a given user by comparing biometric information associated with the given user with biometric information stored by personal wellness device 102, personal computing platform 108, personal wellness platform server 110, and/or other components of personal wellness system 100.

The emergency alert module 508 may be configured to monitor one or more vital signs of a user associated with personal wellness device 102. Examples of vital signs may include one or more of body temperature, heart rate, respiration rate, blood pressure, and/or other vital signs. Monitoring of vital signs may be performed via and/or in conjunction with a heart rate sensor, a blood pressure sensor, and/or other sensors included in or communicatively coupled with personal wellness device 102. The emergency alert module 508 may be configured to provide an emergency alert to an emergency response service responsive to individual ones of the one or more vital signs meeting a threshold condition. For example, an emergency alert may be sent to an emergency response service responsive to the heart rate of a user falling below a threshold rate.

The backup module 510 may be configured to back up information stored by personal wellness device 102. Information stored by personal wellness device 102 may be transmitted to a remote electronic storage configured to electronically store information (e.g., electronic storage 142 of personal computing platform 108 and/or electronic storage 146 of personal wellness platform server 110). The backup module 510 may be configured to perform a backup according to a schedule, responsive to a command received from a user, responsive to information being stored by personal wellness device 102, responsive to personal wellness device 102 becoming communicatively coupled with personal computing platform 108 and/or personal wellness platform server 110, and/or based on other criteria.

The update module 512 to manage updates of software and/or firmware of personal wellness device 102. Software updates and/or firmware updates may be transmitted from personal computing platform 108, personal wellness platform server 110, and/or other components of personal wellness system 100. Software updates and/or firmware updates may be received by personal wellness device 102. Software updates and/or firmware updates may be implemented on processor 140 and/or other components of personal wellness device 102.

The communication module 514 may be configured to provide interpersonal communications capabilities to personal wellness device 102. Examples of interpersonal communications capabilities may include one or more of voice over internet protocol (VoIP), short message service (SMS), multimedia messaging service (MMS), video conferencing, telephony, and/or other interpersonal communication capabilities. The communication module 514 may operate in conjunction with user interface 132 to provide the interpersonal communications capabilities.

Figure 6:
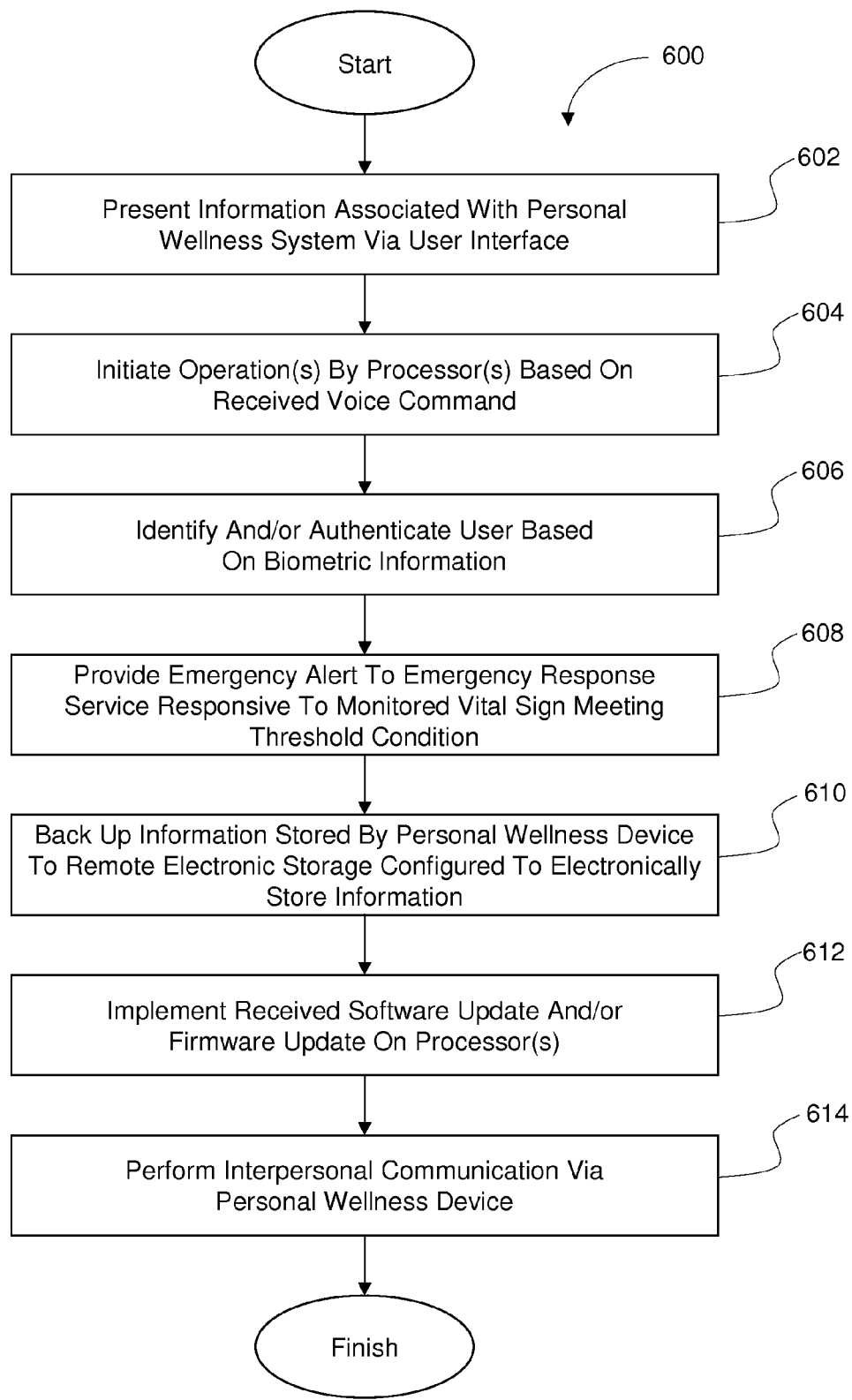
FIG. 6 illustrates a method for facilitating personal wellness via a personal wellness device, in accordance with one or more implementations.

FIG. 6 illustrates a method 600 for facilitating personal wellness via a personal wellness device, in accordance with one or more implementations. The operations of method 600 presented below are intended to be illustrative. In some implementations, method 600 may be accomplished with one or more additional operations not described, and/or without one or more of the operations discussed. Additionally, the order in which the operations of method 600 are illustrated in FIG. 6 and described below is not intended to be limiting.

In some implementations, method 600 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 600 in response to instructions stored electronically on an electronic storage medium. The one or more processing devices may include one or more devices configured through hardware, firmware, and/or software to be specifically designed for execution of one or more of the operations of method 600.

At an operation 602, information associated with personal wellness system 100 may be presented via a user interface (e.g., user interface 132) of a personal wellness device (e.g., personal wellness device 102). Operation 602 may be performed by a presentation module that is the same or similar to presentation module 502, in accordance with some implementations.

At an operation 604, one or more operations by a processor (e.g., processor 500) may be initiated based on a received voice command. Operation 604 may be performed by a voice command module that is the same or similar to voice command module 504, in accordance with one or more implementations.

At an operation 606, a user may be identified and/or authenticated based on biometric information. Operation 606 may be performed by a biometric module that is the same or similar to biometric module 506, in accordance with one or more implementations.

At an operation 608, an emergency alert may be provided to an emergency response service responsive to a monitored vital sign meeting a threshold condition. Operation 608 may be performed by an emergency alert module that is the same or similar to emergency alert module 508, in accordance with one or more implementations.

At an operation 610, information stored by a personal wellness device (e.g., personal wellness device 102) may be backed up to a remote electronic storage configured to electronically store information. In some implementations, information stored at such a remote electronic storage may be transferred to the personal wellness device. This may provide for synchronization of the personal wellness device. Operation 610 may be performed by a backup module that is the same or similar to backup module 510, in accordance with one or more implementations.

At an operation 612, a received software update and/or firmware update may be implemented on one or more processors (e.g., processor 500). Operation 612 may be performed by an update module that is the same or similar to update module 512, in accordance with one or more implementations.

At an operation 614, an interpersonal communication may be performed via a personal wellness device (e.g., personal wellness device 102). The interpersonal communication may include one or more of voice over internet protocol (VoIP), short message service (SMS), multimedia messaging service (MMS), video conferencing, telephony, and/or other interpersonal communication capabilities. Operation 614 may be performed by a communication module that is the same or similar to communication module 514, in accordance with one or more implementations.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A personal wellness device, comprising:
    two housing bodies including a first housing body and a second housing body, the first housing body and the second housing body being movably coupled together by way of a coupling mechanism such that the two housing bodies are reconfigurable between an open configuration and a closed configuration, the two housing bodies being configured to receive compressive force during personal exercise while in the closed configuration;
    a force sensor configured to provide a force output signal that conveys information related to compressive force exerted on the two housing bodies while in the closed configuration, the force sensor being housed by one of the two housing bodies;

a user interface accessible with the two housing bodies in the open configuration, at least a portion of the user interface being inaccessible with the two housing bodies in the closed configuration, the user interface being configured to receive information from a user and provide information to the user, the user interface being housed by one of the two housing bodies; and one or more physical processors housed by one of the two housing bodies, the one or more physical processors being configured by machine-readable instructions to:
effectuate presentation, via the user interface, of information related to the compressive force exerted on the two housing bodies including one or more of magnitude of force, duration of force, a force magnitude profile as a function of time, or a quantity of compressive forces.

2. The personal wellness device of claim 1, wherein the coupling mechanism includes one or more of a hinge, a joint, a swivel, or a sliding track.

3. The personal wellness device of claim 1, further comprising a camera device configured to capture visual data, the camera device being housed by one of the two housing bodies.

4. The personal wellness device of claim 1, further comprising an actuator configured to provide tactile feedback to a user, the actuator being housed by one of the two housing bodies.

5. The personal wellness device of claim 1, further comprising a geo-location sensor configured to provide a location output signal conveying information related to a geo-location of the personal wellness device, the geo-location sensor being housed by one of the two housing bodies.

6. The personal wellness device of claim 1, further comprising a motion sensor configured to provide a motion output signal that conveys information related to a motion and/or orientation of the personal wellness device, the motion sensor being housed by one of the two housing bodies.

7. The personal wellness device of claim 1, further comprising a pedometer configured to provide a step output signal that conveys information related to steps taken by a user carrying the personal wellness device, the pedometer being housed by one of the two housing bodies, wherein the one or more physical processors are further configured by machine-readable instructions to effectuate presentation, via the user interface, of a number of steps taken by the user.

8. The personal wellness device of claim 1, further comprising a heart rate sensor configured to provide a heart rate output signal that conveys information related to a heart rate of a user associated with the personal wellness device, the heart rate sensor being housed by one of the two housing bodies, wherein the one or more physical processors are further configured by machine-readable instructions to effectuate presentation, via the user interface, of the heart rate of the user.

9. The personal wellness device of claim 1, further comprising an electrical muscle stimulation interface configured to removably couple the personal wellness device with an electrode, the electrode being configured to provide electrical muscle stimulation to a user, the electrical muscle stimulation interface being housed by one of the two housing bodies.

10. The personal wellness device of claim 1, further comprising a communications apparatus configured to receive information and/or transmit information from the personal wellness device, the communications apparatus being housed by one of the two housing bodies.

11. The personal wellness device of claim 10, wherein the communications apparatus includes one or both of a wireless communications interface or a wired communications interface.

12. The personal wellness device of claim 10, wherein the communications apparatus is configured to communicatively couple the personal wellness device with a user accessory, the user accessory being separate and distinct from the personal wellness device.

13. The personal wellness device of claim 10, wherein the communications apparatus is configured to communicatively couple the personal wellness device with a blood pressure sensor, the blood pressure sensor being configured to provide a blood pressure output signal that conveys information related to a blood pressure of a user associated with the personal wellness device, and wherein the one or more physical processors are further configured by machine-readable instructions to effectuate presentation, via the user interface, of the blood pressure of the user.

14. The personal wellness device of claim 10, wherein the communications apparatus is configured to communicatively couple the personal wellness device with a computing platform configured to receive and process information related to compressive force exerted on the two housing bodies.

15. The personal wellness device of claim 1, further comprising electronic storage configured to electronically store information, the electronic storage being housed by one of the two housing bodies.

16. The personal wellness device of claim 1, wherein the user interface includes a microphone configured to capture audio information, and wherein the one or more physical processors are further configured by machine-readable instructions to:
receive audio information captured by the microphone that includes a voice command; and
initiate, responsive to reception of the audio information including the voice command, an operation by the one or more physical processors corresponding to the voice command in the received audio information.

17. The personal wellness device of claim 1, further comprising a biometric sensor configured to provide a biometric output signal conveying information related to a biometric feature of a user, and wherein the one or more physical processors are further configured by machine-readable instructions to identify the user based on information derived from the biometric output signal.

18. The personal wellness device of claim 1, wherein the one or more physical processors are further configured by machine-readable instructions to:
monitor one or more vital signs of a user associated with the personal wellness device via a heart rate sensor or a blood pressure sensor included in or communicatively coupled with the personal wellness device; and
provide an emergency alert to an emergency response service responsive to individual ones of the one or more vital signs meeting a threshold condition.

19. The personal wellness device of claim 1, wherein the one or more physical processors are further configured by machine-readable instructions to back up information stored by the personal wellness device by transmitting information stored by the personal wellness device to a remote electronic storage configured to electronically store information.

20. The personal wellness device of claim 1, wherein the one or more physical processors are further configured by machine-readable instructions to:

receive software updates and/or firmware updates; and implement the software updates and/or the firmware updates on the one or more physical processors.

21. The personal wellness device of claim 1, wherein the one or more physical processors are further configured by machine-readable instructions to provide interpersonal communications capabilities to the personal wellness device, the interpersonal communications capabilities including one or more of voice over internet protocol, short message service, multimedia messaging service, video conferencing, or telephony.

22. The personal wellness device of claim 1, wherein the user interface is entirely inaccessible with the two housing bodies in the closed configuration.

* * * * *